(12) United States Patent
Guzmann et al.

(10) Patent No.: US 7,105,478 B2
(45) Date of Patent: Sep. 12, 2006

(54) WATER-SOLUBLE CONTAINER HAVING AT LEAST TWO OPENINGS

(75) Inventors: Marcus Guzmann, Leimen (DE); Geoffrey Robert Hammond, Hull (GB)

(73) Assignee: Reckitt Benckiser (UK) Limited, Slough (GB)

( * ) Notice: Subject to any disclaimer, the term of this patent is extended or adjusted under 35 U.S.C. 154(b) by 38 days.

(21) Appl. No.: 10/475,425

(22) PCT Filed: Apr. 17, 2002

(86) PCT No.: PCT/GB02/01756

§ 371 (c)(1), (2), (4) Date: Oct. 20, 2003

(87) PCT Pub. No.: WO02/085737

PCT Pub. Date: Oct. 31, 2002

(65) Prior Publication Data

US 2004/0118738 A1 Jun. 24, 2004

(30) Foreign Application Priority Data

Apr. 20, 2001 (GB) ................................. 0109710.4

(51) Int. Cl.
*C11D 17/04* (2006.01)

(52) U.S. Cl. .................. 510/439; 510/220; 510/296; 510/406

(58) Field of Classification Search ............... 510/439, 510/220, 296, 406
See application file for complete search history.

(56) References Cited

U.S. PATENT DOCUMENTS

| 3,663,449 | A |   | 5/1972 | Suski et al. ................. 252/174 |
| 3,823,816 | A |   | 7/1974 | Controulis et al. ............ 206/5 |
| 3,929,988 | A | * | 12/1975 | Barth .......................... 424/54 |
| 4,765,916 | A | * | 8/1988 | Ogar et al. .................. 510/513 |
| 4,793,474 | A |   | 12/1988 | Drake .......................... 206/5 |
| 4,973,416 | A | * | 11/1990 | Kennedy .................... 510/296 |
| 5,316,688 | A | * | 5/1994 | Gladfelter et al. .......... 510/224 |
| 6,164,296 | A | * | 12/2000 | Lentsch et al. ............. 134/25.2 |
| 6,228,825 | B1 | * | 5/2001 | Gorlin et al. ............... 510/226 |
| 6,281,183 | B1 | * | 8/2001 | Harbour ..................... 510/406 |
| 6,624,130 | B1 | * | 9/2003 | Giblin et al. ............... 510/297 |

FOREIGN PATENT DOCUMENTS

| DE | 199 41 480 |    | 3/2001 |
| EP | 0 642 987 | A2 | 3/1995 |
| GB | 2 241 485 |    | 9/1991 |
| GB | 2 356 842 |    | 6/2001 |
| WO | WO 89/12587 |  | 12/1989 |
| WO | WO 92/17382 |  | 10/1992 |

* cited by examiner

*Primary Examiner*—Lorna M. Douyon
(74) *Attorney, Agent, or Firm*—Norris McLaughlin & Marcus PA

(57) ABSTRACT

A water-soluble container containing a composition, the container comprising a member having at least two openings positioned on different sides of the member, each opening being closed by a film.

17 Claims, 2 Drawing Sheets

WATER-SOLUBLE CONTAINER HAVING AT LEAST TWO OPENINGS

This application is a 371 of PCT/GB02/01756 filed Apr. 17, 2002 and claims foreign priority from United Kingdom 0109710.4 filed Apr. 20, 2001.

BACKGROUND OF THE INVENTION

1. Field of the Invention

The present invention relates to a water-soluble container and to a process for preparing such container.

2. The Related Art

It is known to package chemical compositions, particularly those which may be of a hazardous or irritant nature, in films, particularly water soluble films. Such containers can simply be added to water in order to dissolve or disperse the contents of the container into the water.

For example, WO 89/12587 discloses a package which comprises an envelope of a water soluble material which comprises a flexible wall and a water-soluble heat seal. The package may contain an organic liquid comprising, for example, a pesticide, fungicide, insecticide or herbicide.

WO 92/17382 discloses a package containing an agrochemical comprising a first sheet of non-planar water-soluble or water-dispersible material and a second sheet of water-soluble or water-dispersible material superposed on the first sheet and sealed to it.

Such packages, however, can only be of a fairly simple shape. They may also give an impression of a lack of rigidity. Thus they may be considered unattractive by a consumer. The packages disclosed in WO 89/12587 are produced by the vertical form-fill-seal method, which can only produce packages having a flat or rounded envelope-like shape. The packages produced in WO 92/17382 can have more complex shapes since they are produced by thermoforming.

However, the range of shapes is still limited and it is difficult to provide the package with a degree of rigidity if this is desired.

SUMMARY OF THE INVENTION

The present invention provides a water-soluble container containing a composition, said container comprising a member having at least two openings positioned on different sides of the member, each opening being closed by a film. The term "water-soluble" includes water-dispersible.

The term "water-soluble" when used herein means that when used in a washing machine, such as a fabric or dish washing machine, the water-soluble aspects of the article are substantially (greater than 70%, ideally greater than 85%) dissolved or dispersed into the water. This can be tested by placing the article in 10 liters of agitated water at 45 C. for 40 minutes and measuring any undissolved or non-disintegrated pieces of the parts of the article, which are water-soluble, that are left.

The present invention also provides the process for preparing a container that is defined above which comprises forming the member having at least two openings on different sides, optionally closing at least one of the openings with a film, filling the member with a composition and closing each remaining opening with a film.

Since the containers of the present invention contain a member which can provide a degree of strength to the containers, they can have a greater degree of rigidity than the containers of the prior art discussed above.

Furthermore they can have an attractive, uniform appearance which does not vary between different containers. It is also easily possible to introduce two or more compartments to separate mutually incompatible ingredients. The container can also have almost any shape that might be useful. Furthermore it is possible to use sealing films having different dissolution characteristics allowing the containers to release different compositions at different temperatures.

DETAILED DESCRIPTION OF THE INVENTION

The containers of the present invention can have a more rigid structure than the containers discussed above. In particular their main strength is derived from the member having at least two openings. This member can be fairly rigid, especially when it is formed by injection moulding. Although it might be possible to prepare a whole container by injection moulding, since this produces walls which are thicker than films, such a container could take too long to dissolve. Furthermore the walls tend to be rather opaque which means the contents cannot easily be seen. Accordingly, in the containers of the present invention, it is only the member providing the general strength to the container which needs to be rigid. This member has at least two openings positioned on different sides of the member which are closed by a film, which is thinner than the thickness of the member. This ensures that the container can release its contents in a relatively short time after it has been added to water. The remainder of the container made up of the member can dissolve at a later stage. The member may be formed by, for example, casting or by moulding, for example by injection moulding. The member provides the general shape to the container. It may, therefore, be in the form of a framework, particularly in the form of a wire framework forming the edges of the container.

For example, the member can be in the form of a wire framework making up the edges of a standard geometrical shape such as cube, cuboid, rhomboid, pyramid, dodecahedron or cylinder. The wire making up the framework may have any desired cross-section, for example square, rectangular or circular.

One or more of the faces of such geometrical shapes may, however, be fully or partly closed in the member. Thus, for example, two opposing solid faces may be formed, preferably in opposite sides of the geometrical shapes such as a cube, cuboid or cylinder, and the remaining faces left open. The solid faces may be perforated if desired to allow for quicker release of the contents of the container.

The member must, according to the present invention, have at least two openings positioned on different sides of the member. The member may, for example, have two, three, four, five or six or more openings depending on its shape.

Figure 1:
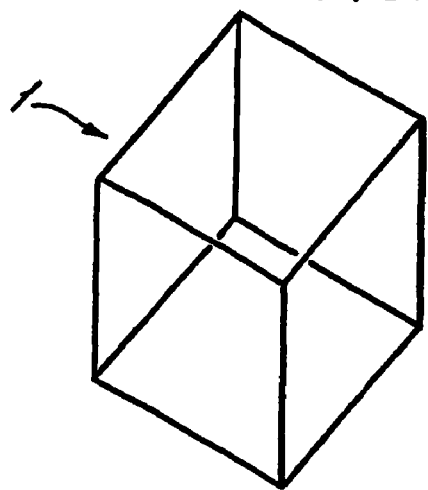
FIG. 1 illustrates framework members consisting of a wire framework having a certain geometric shape.
Figure 2:
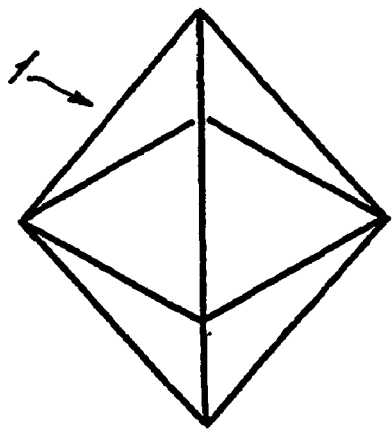
FIG. 2 illustrates framework members consisting of a wire framework having a certain geometric shape.
Figure 3:
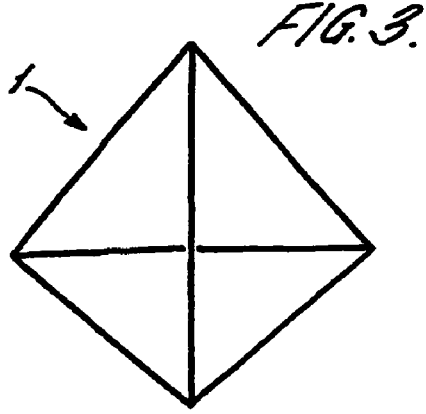
FIG. 3 illustrates framework members consisting of a wire framework having a certain geometric shape.
Figure 4:
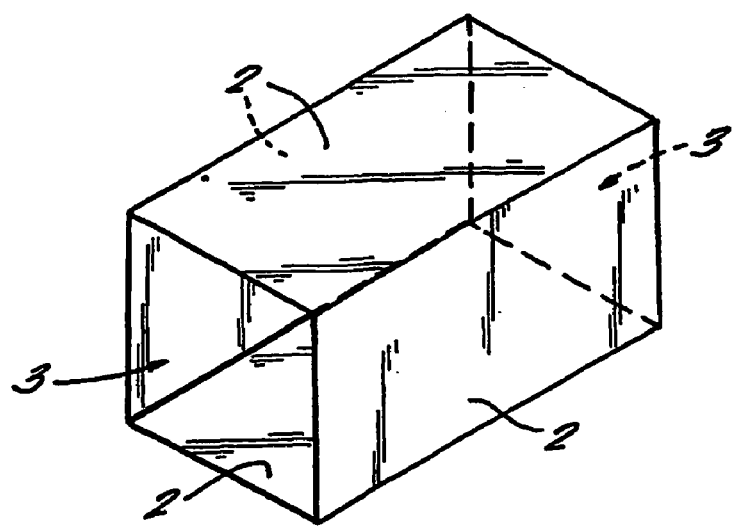
FIG. 4 illustrates a framework member consisting of a cuboid having four solid faces and two openings at opposite ends of the cuboid.
Figure 5:
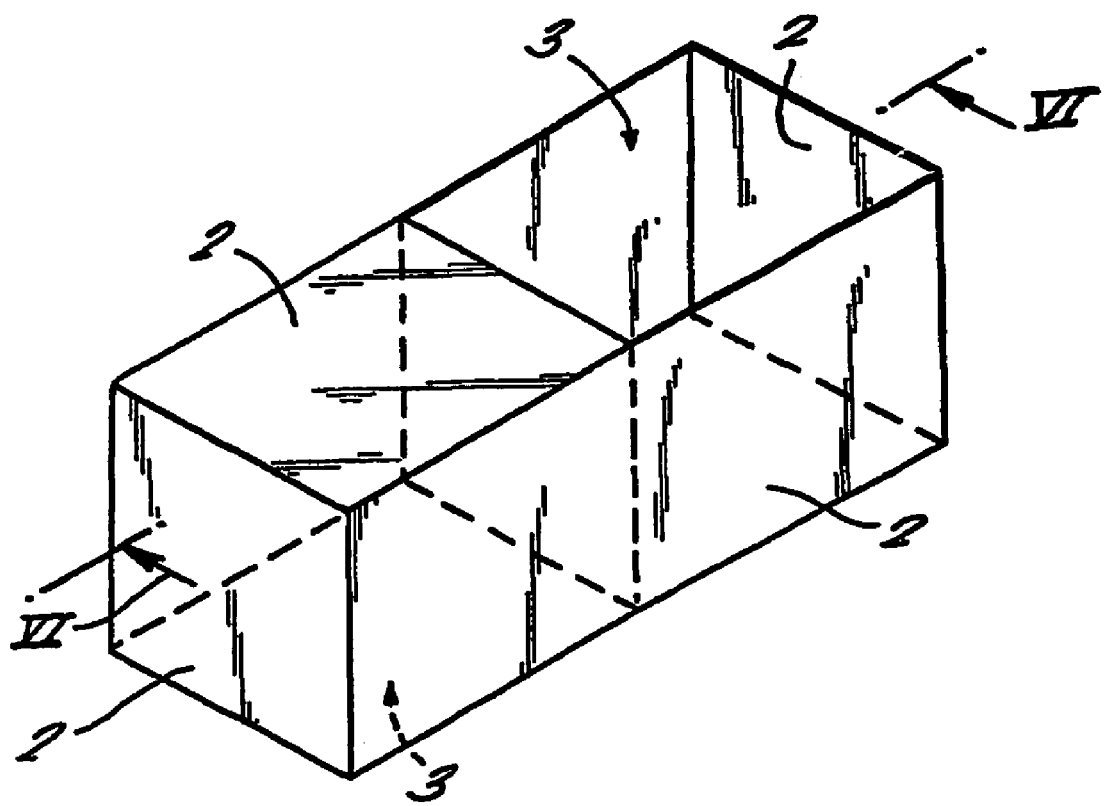
FIG. 5 illustrates a cuboid member which is split into two compartments with solid faces and two openings on opposite sides of the member.

Examples of suitable members are shown in the attached drawings. FIGS. 1, 2 and 3 illustrate framework members consisting of a wire framework 1. FIG. 4 illustrates a member consisting of a cuboid with four solid faces 2 and two openings 3 at opposite ends of the cuboid. FIG. 5 illustrates a cuboid member which is split into two compartments. The member consists of a cuboid with solid faces 2 and two openings 3 on opposite sides of the member.

Figure 6:
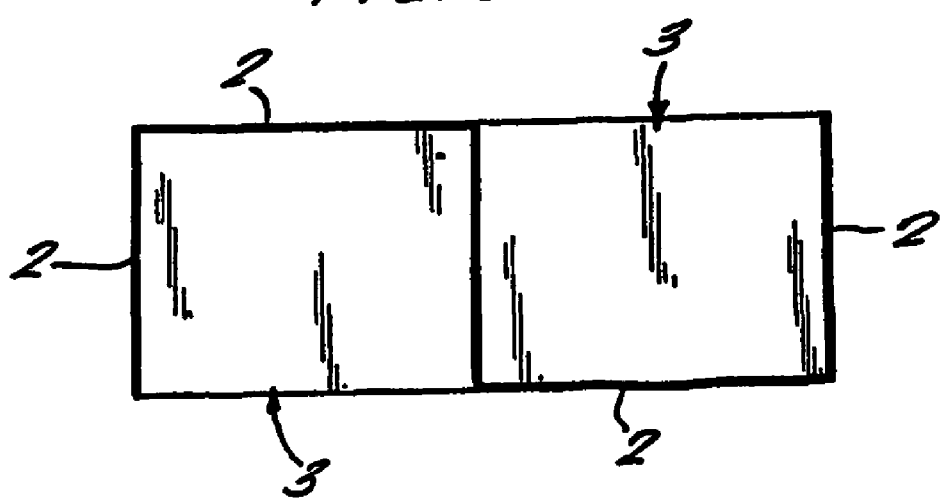
FIG. 6 illustrates a cross-section of the member of FIG. 5 taken along VI—VI.

FIG. 6 illustrates a cross-section of the member of FIG. 5 taken along the line VI of FIG. 5. One compartment of the member can be filled with a composition and the opening closed by a film. The member can then be turned upside down and the process repeated to fill and seal the other compartment.

The walls of the member, or the wire, generally have a thickness greater than 100 µm, for example greater than 150 µm or greater than 200 µm, 300 µm, 500 µm, 750 µm or 1 mm. Desirably, however, the walls have a thickness of from 200 to 400 µm, and the wire framework has a wire cross-section thickness of from 0.5 to 2 mm, especially about 1 mm.

The member comprises, and preferably consists essentially of, or consists of, a water-soluble polymer and plasticizers and/or lubricants. The polymer has sufficient strength to ensure that the container has a degree of rigidity and is preferably self-supporting.

Examples of water-soluble polymers which may be used are poly(vinyl alcohol) (PVOH), cellulose derivatives such as hydroxypropyl methyl cellulose (HPMC) and gelatin. An example of a preferred PVOH is ethoxylated PVOH. The PVOH may be partially or fully alcoholised or hydrolysed. For example it may be from 40 to 100%, preferably from 70 to 92%, more preferably about 88% or about 92%, alcoholised or hydrolysed. The degree of hydrolysis is known to influence the temperature at which the PVOH starts to dissolve in water. 88% hydrolysis corresponds to a film soluble in cold (i.e. room temperature) water, whereas 92% hydrolysis corresponds to a film soluble in warm water.

It is possible for suitable additives such as plasticizers or lubricants to be included in the polymer. Plasticizers are generally used in an amount of up to 20 wt %, for example, from 15 to 20 wt %, lubricants are generally used in an amount of 0.5 to 5 wt % and the polymer is generally therefore used in an amount of 75 to 84.5 wt %, based on the total amount of the moulding composition. Suitable plasticizers are, for example, pentaerthyritol such as dipentaerthyritol, sorbitol, mannitol, glycerine and glycols such as glycerol, ethylene glycol and polyethylene glycol.

Solids such as talc, stearic acid, magnesium stearate, silicon dioxide, zinc stearate and colloidal silica may also be used. A preferred PVOH which is already in a form suitable for injection moulding is sold in the form of granules under the name CP1210T05 by Soltec Developpment S.A. Paris, France.

The PVOH may be moulded at temperatures of, for example, from 180 to 220° C., depending upon the formulation selected and the melt flow index required.

In order to complete the container, the openings in the member must be closed by a film, although it is possible for some of the openings, for example 1, 2, 3 or 4 openings, to be closed by other means, such as by injection moulded closures. A single film can be used to close all the openings or the openings can be closed by two or more films. For example, each opening may be sealed by a separate film.

Any method may be used to close the openings in the member by the film. For example the member can simply be wrapped in the film. If it is desired to have an attractive appearance with a smooth film, the film can be shrink-wrapped around the member. This can be done by pre-stretching the film, for example by biaxially orientation, and then heating it to shrink it around the member. In a preferred method of the present invention, however, the film is thermoformed around the member.

In this method a pocket is produced in the film. Generally, unless the film is sufficiently thick or the internal member has a sufficient thickness on which to seal the lidding film, the pocket is surrounded by a sealing portion. The member is then placed in the pocket, the desired composition is added to the pocket and the pocket sealed by placing a film on top of the filled pocket and across the sealing portion and sealing the films together at the sealing portion. If the composition is liquid, it is also possible to place the composition in the pocket before the member.

The pocket may be formed by, for example, vacuum forming or thermoforming. For example, in a thermoforming process the film may be drawn down or blown down into a mould. Thus, for example, the film is heated to the thermoforming temperature using a thermoforming heater plate assembly, and then drawn down under vacuum or blown down under pressure into the mould. Plug-assisted thermoforming and pre-stretching the film, for example by blowing the film away from the mould before thermoforming, may, if desired, be used. One skilled in the art can choose an appropriate temperature, pressure or vacuum and dwell time to achieve an appropriate pocket. The amount of vacuum or pressure and the thermoforming temperature used depend on the thickness and porosity of the film and on the polymer or mixture of polymers being used. Thermoforming of PVOH films is known and described in, for example, WO 00/55045.

A suitable forming temperature for PVOH or ethoxylated PVOH is, for example, from 90 to 130° C., especially 90 to 120° C. A suitable forming pressure is, for example, 69 to 138 kPa (10 to 20 p.s.i.), especially 83 to 117 kPa (12 to 17 p.s.i.). A suitable forming vacuum is 0 to 4 kPa (0 to 40 mbar), especially 0 to 2 kPa (0 to 20 mbar). A suitable dwell time is, for example, 0.4 to 2.5 seconds, especially 2 to 2.5 seconds.

While desirably conditions are chosen within the above ranges, it is possible to use one or more of these parameters outside the above ranges, although it may be necessary to compensate by changing the values of the other two parameters.

The member is then added to the pocket by pick and placing, for example by using robots. Desirably the member has a height which is greater than the height of the thermo-formed pocket and therefore stretches the lidding film when it is applied. This may head to a more attractive appearance for the final container, particularly if that film shrinks back over the member, for example if the film is PVOH.

The pocket is then filled with the desired first composition. The pocket may be completely filled or only partially filled. The composition may be a solid. For example, it may be a particulate or granulated solid, or a tablet. It may also be a liquid, which may be thickened or gelled if desired. The liquid composition may be non-aqueous or aqueous, for example comprising less than or more than 5% total or free water. The composition may have more than one phase. For example it may comprise an aqueous composition and a liquid composition which is immiscible with the aqueous composition. It may also comprise a liquid composition and a separate solid composition, for example in the form of a ball, pill or speckles.

One or more water-soluble films are then placed on the filled pocket and sealed to the sealing portions. A single film is generally used, but two or more films may be used if desired particularly if it is desired to seal different openings in the member with different films.

The films may be sealed together by any suitable means, for example by means of an adhesive or by heat sealing. Other methods of sealing include infra-red, radio frequency, ultrasonic, laser, solvent, vibration and spin welding. An adhesive such as an aqueous solution of PVOH may also be used. The seal desirably is water-soluble if the containers are water-soluble.

If heat sealing is used, a suitable sealing temperature is, for example, 120 to 195° C., for example 140 to 150° C. A suitable sealing pressure is, for example, from 250 to 600 kPa. Examples of sealing pressures are 276 to 552 kPa (40 to 80 p.s.i.), especially 345 to 483 kPa (50 to 70 p.s.i.) or 400 to 800 kPa (4 to 8 bar), especially 500 to 700 kPa (5 to 7 bar) depending on the heat sealing machine used. Suitable sealing dwell times are 0.4 to 2.5 seconds.

One skilled in the art can use an appropriate temperature, pressure and dwell time to achieve a seal of the desired integrity. While desirably conditions are chosen within the above ranges, it is possible to use one or more of these parameters outside the above ranges, although it would might be necessary to compensate by changing the values of the other two parameters.

The thickness of the film closing the openings is desirably 25 to 150 μm, preferably 30 to 100 μm, more preferably 40 to 80 μm. Thus, the thickness of the film used to produce the pocket when thermoforming is used, is preferably 40 to 300 μm, more preferably 80 to 200 μm, especially 100 to 160 μm, more especially 100 to 150 μm and most especially 120 to 150 μm. Thicker film is required when thermoforming is used because the film thins when it is stretched during the thermoforming process.

When the member is simply wrapped in the film, the film desirably has a thickness of 20 to 160 μm, preferably 40 to 100 μm, more preferably 40 to 80 μm.

The films may be single films, or laminated films as disclosed in GB-A-2,244,258. While a single film may have pinholes, the two or more layers in a laminate are unlikely to have pinholes which coincide.

The layers in a laminate may be the same or different. Thus they may each comprise the same polymer or a different polymer. For a water-soluble laminated film, each of the layers should be water-soluble.

The film may be produced by any process, for example by extrusion and blowing or by casting. The film may be unoriented, monoaxially oriented or biaxially oriented. If the layers in the film are oriented, they usually have the same orientation, although their planes of orientation may be different if desired.

The film is preferably transparent or translucent so that the contents in the container can be seen. The member may also be transparent or translucent. It may also be coloured such that it can easily be seen, and hence provide an attractive appearance.

The container may comprise a single compartment or may comprise two or more compartments, such as two, three or four or more compartments. These compartments may either be formed from the member or from the films closing the openings in the member.

It is a simple matter to incorporate the different compartments in the member by using a mould of an appropriate shape and form. The compartments are separated by injection moulded walls.

Alternatively, or as well as, the film may contain further compartments. For example, a film used to close one or more of the openings may itself have a compartment therein containing a composition.

The compartment in the film may be formed by any technique. For example it can be formed by vertical form fill sealing a second composition within a film, such as by the process described in WO 89/12587.

However, it is preferred to use a vacuum forming or thermoforming techniques, such as that previously described. Thus, for example, a pocket surrounded by a sealing portion is formed in a film, the pocket is filled with the second composition, a film is placed on top of the filled pocket and across the sealing portion and the films are sealed together at the sealing portion. In general, however, the film placed on top of the filled pocket to form the compartment does not itself comprise a further compartment.

Further details of this thermoforming process are generally the same as those given above. All of the above details are incorporated by reference, except that the thickness of the film comprising the second compartment may also be less than the thickness of the film making up the first compartment of the container of the present invention, because the film is not subjected to as much localised stretching in the thermoforming step. It is also desirable to have a thickness which is less than that of the film used to form the first compartment to ensure a sufficient heat transfer through the film to soften the base web if heat sealing is used.

If the containers of the present invention contain two or more compartments, they can have a particularly attractive appearance since they contain two compositions held in a fixed position in relation to each other. The compositions can be easily differentiated to accentuate their difference. For example, the compositions can have a different physical appearance, or can be coloured differently. Thus, for example, the containers can have an appearance of a fried egg or eyeball.

If the container contains two to more different compartments, it is possible to ensure that the compositions are released at different times. Thus, for instance, one composition can be released immediately the container is added to water, whereas the other may be released later. This may be achieved by closing the opening of the compartment containing one of the compositions with a film which takes longer to dissolve. It may also be achieved by choosing films which dissolve at different temperatures, for example at the different temperatures encountered during the cycle of a laundry or dish washing machine.

The composition may be any composition which is intended to be released in an aqueous environment. Thus, for example, it may be an agrochemical composition such as a plant protection agent, for instance a pesticide such as an insecticide, fungicide, herbicide, acaricide, or nematocide, a plant growth regulator or a plant nutrient. Such compositions are generally packaged in amounts of from 0.1 g to 7 kg, preferably 1 to 5 kg, when in solid form. When in liquid or gelled form, such compositions are generally packaged in amounts of from 1 ml to 10 liters, preferably 0.1 to 6 liters, especially from 0.5 to 1.5 liters.

The composition may also be a fabric care, surface care or dishwashing composition. Thus, for example, it may be a dishwashing, water-sofetning, laundry or detergent composition, or a rinse aid. Such compositions may be suitable for use in a domestic washing machine. The composition may also be a disinfectant, antibacterial or antiseptic composition, or a refill composition for a trigger-type spray. Such compositions are generally packaged in amounts of from 5 to 100 g, especially from 15 to 40 g. For example, a dishwashing composition may weigh from 15 to 30 g, a water-softening composition may weigh from 15 to 40 g.

The composition, if in liquid form, may be anhydrous or comprise water, for example at least 5 wt %, preferably at least 10 wt %, water based on the weight of the aqueous composition. Desirably the composition contains less than 80 wt % water.

The remaining ingredients of the composition depend on the use of the composition. Thus, for example, the composition may contain surface active agents such as an anionic, nonionic, cationic, amphoteric or zwitterionic surface active agents or mixtures thereof.

Examples of anionic surfactants are straight-chained or branched alkyl sulfates and alkyl polyalkoxylated sulfates, also known as alkyl ether sulfates. Such surfactants may be produced by the sulfation of higher $C_8$–$C_{20}$ fatty alcohols.

Examples of primary alkyl sulfate surfactants are those of formula:

$$ROSO_3^-M^+$$

wherein R is a linear $C_8$–$C_{20}$ hydrocarbyl group and M is a water-solubilising cation. Preferably R is $C_{10}$–$C_{16}$ alkyl, for example $C_{12}$–$C_{14}$, and M is alkali metal such as lithium, sodium or potassium.

Examples of secondary alkyl sulfate surfactants are those which have the sulfate moiety on a "backbone" of the molecule, for example those of formula:

$$CH_3(CH_2)_n(CHOSO_3^-M^+)(CH_2)_mCH_3$$

wherein m and n are independently 2 or more, the sum of m+n typically being 6 to 20, for example 9 to 15, and M is a water-solubilising cation such as lithium, sodium or potassium.

Especially preferred secondary alkyl sulfates are the (2,3) alkyl sulfate surfactants of formulae:

$$CH_3(CH_2)_x(CHOSO_3^-M^+)CH_3 \text{ and}$$

$$CH_3(CH_2)_x(CHOSO_3^-M^+)CH_2CH_3$$

for the 2-sulfate and 3-sulfate, respectively. In these formulae x is at least 4, for example 6 to 20, preferably 10 to 16. M is cation, such as an alkali metal, for example lithium, sodium or potassium.

Examples of alkoxylated alkyl sulfates are ethoxylated alkyl sulfates of the formula:

$$RO(C_2H_4O)_nSO_3^-M^+$$

wherein R is a $C_8$–$C_{20}$ alkyl group, preferably $C_{10}$–$C_{18}$ such as a $C_{12}$–$C_{16}$, n is at least 1, for example from 1 to 20, preferably 1 to 15, especially 1 to 6, and M is a salt-forming cation such as lithium, sodium, potassium, ammonium, alkylammonium or alkanolammonium. These compounds can provide especially desirable fabric cleaning performance benefits when used in combination with alkyl sulfates.

The alkyl sulfates and alkyl ether sulfates will generally be used in the form of mixtures comprising varying alkyl chain lengths and, if present, varying degrees of alkoxylation.

Other anionic surfactants which may be employed are salts of fatty acids, for example $C_8$–$C_{18}$ fatty acids, especially the sodium or potassium salts, and alkyl, for example $C_8$–$C_{18}$, benzene sulfonates.

Examples of nonionic surfactants are fatty acid alkoxylates, such as fatty acid ethoxylates, especially those of formula:

$$R(C_2H_4O)_nOH$$

wherein R is a straight or branched $C_8$–$C_{16}$ alkyl group, preferably a $C_9$–$C_{15}$, for example $C_{10}$–$C_{14}$, alkyl group and n is at least 1, for example from 1 to 16, preferably 2 to 12, more preferably 3 to 10.

The alkoxylated fatty alcohol nonionic surfactant will frequently have a hydrophilic-lipophilic balance (HLB) which ranges from 3 to 17, more preferably from 6 to 15, most preferably from 10 to 15.

Examples of fatty alcohol ethoxylates are those made from alcohols of 12 to 15 carbon atoms and which contain about 7 moles of ethylene oxide. Such materials are commercially marketed under the trademarks Neodol 25-7 and Neodol 23-6.5 by Shell Chemical Company. Other useful Neodols include Neodol 1-5, an ethoxylated fatty alcohol averaging 11 carbon atoms in its alkyl chain with about 5 moles of ethylene oxide; Neodol 23-9, an ethoxylated primary $C_{12}$–$C_{13}$ alcohol having about 9 moles of ethylene oxide; and Neodol 91-10, an ethoxylated $C_9$–$C_{11}$ primary alcohol having about 10 moles of ethylene oxide.

Alcohol ethoxylates of this type have also been marketed by Shell Chemical Company under the Dobanol trademark. Dobanol 91-5 is an ethoxylated $C_9$–$C_{11}$ fatty alcohol with an average of 5 moles ethylene oxide and Dobanol 25-7 is an ethoxylated $C_{12}$–$C_{15}$ fatty alcohol with an average of 7 moles of ethylene oxide per mole of fatty alcohol.

Other examples of suitable ethoxylated alcohol nonionic surfactants include Tergitol 15-S-7 and Tergitol 15-S-9, both of which are linear secondary alcohol ethoxylates available from Union Carbide Corporation. Tergitol 15-S-7 is a mixed ethoxylated product of a $C_{11}$–$C_{15}$ linear secondary alkanol with 7 moles of ethylene oxide and Tergitol 15-S-9 is the same but with 9 moles of ethylene oxide.

Other suitable alcohol ethoxylated nonionic surfactants are Neodol 45-11, which is a similar ethylene oxide condensation products of a fatty alcohol having 14–15 carbon atoms and the number of ethylene oxide groups per mole being about 11. Such products are also available from Shell Chemical Company.

Further nonionic surfactants are, for example, $C_{10}$–$C_{18}$ alkyl polyglycosides, such s $C_{12}$–$C_{16}$ alkyl polyglycosides, especially the polyglucosides. These are especially useful when high foaming compositions are desired. Further surfactants are polyhydroxy fatty acid amides, such as $C_{10}$–$C_{18}$ N-(3-methoxypropyl) glycamides and ethylene oxide-propylene oxide block polymers of the Pluronic type.

Examples of cationic surfactants are those of the quaternary ammonium type.

The total content of surfactants in the composition is desirably 60 to 95 wt %, especially 75 to 90 wt %. Desirably an anionic surfactant is present in an amount of 50 to 75 wt %, the nonionic surfactant is present in an amount of 5 to 50 wt %, and/or the cationic surfactant is present in an amount of from 0 to 20 wt %. The amounts are based on the total solids content of the composition, i.e. excluding any solvent which may be present.

The compositions, particularly when used as laundry washing or dishwashing compositions, may also independently comprise enzymes, such as protease, lipase, amylase, cellulase and peroxidase enzymes. Such enzymes are commercially available and sold, for example, under the registered trade marks Esperase, Alcalase and Savinase by Nova Industries A/S and Maxatase by International Biosynthetics, Inc. Desirably the enzymes are independently present in the primary or secondary compositions in an amount of from 0.5 to 3 wt %, especially 1 to 2 wt %, when added as commecial preparations they are not pure and this represents an equivalent amount of 0.005 to 0.5 wt % of pure enzyme.

The compositions may, if desired, independently comprise a thickening agent or gelling agent. Suitable thickeners are polyacrylate polymers such as those sold under the trade mark CARBOPOL, or the trade mark ACUSOL by Rohm and Haas Company. Other suitable thickeners are xanthan gums. The thickener, if present, is generally present in an amount of from 0.2 to 4 wt %, especially 0.5 to 2 wt %.

Compositions used in dishwashing an laundry independently usually comprise a detergency builder. The builders counteract the effects of calcium, or other ion, water hardness encountered. Examples of such materials are citrate, succinate, malonate, carboxymethyl succinate, carboxylate, polycarboxylate and polyacetyl carboxylate salts, for example with alkali metal or alkaline earth metal cations, or the corresponding free acids. Specific examples are sodium, potassium and lithium salts of oxydisuccinic acid, mellitic acid, benzene polycarboxylic acids, $C_{10}$–$C_{22}$ fatty acids and citric acid. Other examples are organic phosphonate type sequestering agents such as those sold by Monsanto under the trade mark Dequest and alkylhydroxy phosphonates. Citrate salts and $C_{12}$–$C_{18}$ fatty acid soaps are preferred. Further builders are; phosphates such as sodium, potassium or ammonium salts of mono-, di- or tri-poly or oligophosphates; zeolites; silicates, amorphous or structured, such as sodium, potassium or ammonium salts.

Other suitable builders are polymers and copolymers known to have builder properties. For example, such materials include appropriate polyacrylic acid, polymaleic acid, and polyacrylic/polymaleic and copolymers and their salts, such as those sold by BASF under the trade mark Sokalan.

The builder is desirably present in an amount of up to 90 wt %, preferably 15 to 90 wt %, more preferable 15 to 75 wt %, relative to the total weight of the composition. Further details of suitable components are given in, for example, EP-A-694,059, EP-A-518,720 and WO 99/06522.

The compositions can also independently optionally comprise one or more additional ingredients. These include conventional detergent composition components such as further surfactants, bleaches, bleach enhancing agents, builders, suds boosters or suds suppressors, anti-tarnish and anti-corrosion agents, organic solvents, co-solvents, phase stabilisers, emulsifying agents, preservatives, soil suspending agents, soil release agents, germicides, pH adjusting agents or buffers, non-builder alkalinity sources, chelating agents, clays such as smectite clays, enzyme stabilizers, anti-limescale agents, colourants, dyes, hydrotropes, dye transfer inhibiting agents, brighteners, and perfumes. If used, such optional ingredients will generally constitute preferably no more than 15 wt %, for example from 1 to 6 wt %, the total weight of the compositions.

Compositions which comprise an enzyme may optionally contain materials which maintain the stability of the enzyme. Such enzyme stabilizers include, for example, polyols such as propylene glycol, boric acid and borax. Combinations of these enzyme stabilizers may also be employed. If utilized, the enzyme stabilizers generally constitute from 0.1 to 5 wt %, ideally 0.1 to 1 wt % of the compositions.

The compositions may independently optionally comprise materials which serve as phase stabilizers and/or co-solvents. Example are $C_1$–$C_3$ alcohols such as methanol, ethanol and propanol. $C_1$–$C_3$ alkanolamines such as mono-, di- and triethanolamines can also be used, by themselves or in combination with the alcohols. The phase stabilizers and/or co-solvents can, for example, constitute 0 to 1 wt %, preferably 0.1 to 0.5 wt %, of the composition.

The compositions may independently optionally comprise components which adjust or maintain the pH of the compositions at optimum levels. The pH may be from, for example, 1 to 13, such as 8 to 11 depending on the nature of the composition. For example a dishwashing composition desirably has a pH of 8 to 11, a laundry composition desirable has a pH of 7 to 9, and a water-softening composition desirably has a pH of 7 to 9. Examples of pH adjusting agents are NaOH and citric acid.

The above examples may be used for dish or fabric washing. In particular dish washing formulations are preferred which are adapted to be used in automatic dish washing machines. Due to their specific requirements specialised formulation are required and these are illustrated below Amounts of the ingredients can vary within wide ranges, however preferred automatic dishwashing detergent compositions herein (which typically have a 1% aqueous solution pH of above 8, more preferably from 9.5 to 12, most preferably from 9.5 to 10.5) are those wherein there is present: from 5% to 90%, preferably from 5% to 75%, of builder; from 0.1% to 40%, preferably from 0.5% to 30%, of bleaching agent; from 0.1% to 15%, preferably from 0.2% to 10%, of the surfactant system; from 0.0001% to 1%, preferably from 0.001% to 0.05%, of a metal-containing bleach catalyst; and from 0.1% to 40%, preferably from 0.1% to 20% of a water-soluble silicate. Such fully-formulated embodiments typically further comprise from 0.1% to 15% of a polymeric dispersant, from 0.01% to 10% of a chelant, and from 0.00001% to 10% of a detersive enzyme, though further additional or adjunct ingredients may be present. Detergent compositions herein in granular form typically limit water content, for example to less than 7% free water, for better storage stability.

Non-ionic surfactants useful in ADW (Automatic Dish Washing) compositions of the present invention desirably include surfactant(s) at levels of from 2% to 60% of the composition. In general, bleach-stable surfactants are preferred. Non-ionic surfactants generally are well known, being described in more detail in Kirk Othmer's Encyclopedia of Chemical Technology, 3rd Ed., Vol. 22, pp. 360–379, "Surfactants and Detersive Systems", incorporated by reference herein.

Preferably the ADW composition comprises at least one non-ionic surfactant. One class of non-ionics are ethoxylated non-ionic surfactants prepared by the reaction of a monohydroxy alkanol or alkylphenol with 6 to 20 carbon atoms with preferably at least 12 moles particularly preferred at least 16 moles, and still more preferred at least 20 moles of ethylene oxide per mole of alcohol or alkylphenol.

Particularly preferred non-ionic surfactants are the non-ionic from a linear chain fatty alcohol with 16–20 carbon atoms and at least 12 moles particularly preferred at least 16 and still more preferred at least 20 moles of ethylene oxide per mole of alcohol.

According to one preferred embodiment of the non-ionic surfactant additionally comprise propylene oxide units in the molecule. Preferably this PO units constitute up to 25% by weight, preferably up to 20% by weight and still more preferably up to 15% by weight of the overall molecular weight of the non-ionic surfactant. Particularly preferred surfactants are ethoxylated mono-hydroxy alkanols or alkylphenols, which additionally comprises polyoxyethylene-polyoxypropylene block copolymer units. The alcohol or alkylphenol portion of such surfactants constitutes more than 30%, preferably more than 50%, more preferably more than 70% by weight of the overall molecular weight of the non-ionic surfactant.

Another class of non-ionic surfactants includes reverse block copolymers of polyoxyethylene and polyoxypropylene and block copolymers of polyoxyethylene and polyoxypropylene initiated with trimethylolpropane.

Another preferred non-ionic surfactant can be described by the formula:

$$R^1O[CH_2CH(CH_3)O]_x[CH_2CH_2O]_y[CH_2CH(OH)R^2]$$

wherein $R^1$ represents a linear or branched chain aliphatic hydrocarbon group with 4–18 carbon atoms or mixtures thereof, $R^2$ represents a linear or branched chain aliphatic hydrocarbon rest with 2–26 carbon atoms or mixtures thereof, x is a value between 0.5 and 1.5 and y is a value of at least 15.

Another group of preferred nonionic surfactants are the end-capped polyoxyalkylated non-ionics of formula:

$$R^1O[CH_2CH(R^3)O]_x[CH_2]_kCH(OH)[CH_2]_jOR^2$$

wherein $R^1$ and $R^2$ represent linear or branched chain, saturated or unsaturated, aliphatic or aromatic hydrocarbon groups with 1–30 carbon atoms, $R^3$ represents a hydrogen atom or a methyl, ethyl, n-propyl, iso-propyl, n-butyl, 2-butyl or 2-methyl-2-butyl group, x is a value between 1 and 30 and, k and j are values between 1 and 12, preferably between 1 and 5, When the value of x is $\geq 2$ each $R^3$ in the formula above can be different. $R^1$ and $R^2$ are preferably linear or branched chain, saturated or unsaturated, aliphatic or aromatic hydrocarbon groups with 6–22 carbon atoms, where group with 8 to 18 carbon atoms are particularly preferred. For the group $R^3$ H, methyl or ethyl are particularly preferred. Particularly preferred values for x are comprised between 1 and 20, preferably between 6 and 15.

As described above, in case $x \geq 2$, each $R^3$ in the formula can be different. For instance, when x=3, the group $R^3$ could be chosen to build ethylene oxide ($R^3$=H) or propylene oxide ($R^3$=methyl) units which can be used in every single order for instance (PO)(EO)(EO), (EO)(PO)(EO), (EO)(EO)(PO), (EO)(EO)(EO), (PO)(EO)(PO), (PO)(PO)(EO) and (PO)(PO)(PO). The value 3 for x is only an example and bigger values can be chosen whereby a higher number of variations of (EO) or (PO) units would arise.

Particularly preferred end-capped polyoxyalkylated alcohols of the above formula are those where k=1 and j=1 originating molecules of simplified formula:

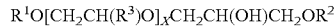

$$R^1O[CH_2CH(R^3)O]_xCH_2CH(OH)CH_2OR^2$$

The use of mixtures of different non-ionic surfactants is particularly preferred in ADW formulations for example mixtures of alkoxylated alcohols and hydroxy group containing alkoxylated alcohols.

If the containers of the present invention contain two or more compositions, the compositions may be the same or different. If they are different they may, nevertheless, have one or more individual components in common.

The primary composition and the secondary composition may be appropriately chosen depending on the desired use of the article.

If the article is for use in laundry washing, the primary composition may comprise, for example, a detergent, and the secondary composition may comprise a bleach, stain remover, water-softener, enzyme or fabric conditioner. The article may be adapted to release the compositions at different times during the laundry wash. For example, a bleach or fabric conditioner is generally released at the end of a wash, and a water-softener is generally released at the start of a wash. An enzyme may be released at the start or the end of a wash.

If the article is for use as a fabric conditioner, the primary composition may comprise a fabric conditioner and the secondary component may comprise an enzyme which is released before or after the fabric conditioner in a rinse cycle.

If the article is for use in dish washing the primary composition may comprise a detergent and the secondary composition may comprise a water-softener, salt, enzyme, rinse aid, bleach or bleach activator. The article may be adapted to release the compositions at different times during the laundry wash. For example, a rinse aid, bleach or bleach activator is generally released at the end of a wash, and a water-softener, salt or enzyme is generally released at the start of a wash.

If the container contains an aqueous liquid having a relatively higher water content, it may be necessary to take steps to ensure that the liquid does not attack the water-soluble polymer if it is soluble in cold water (20° C.), or water at a temperature or up to say 35° C. Steps may be taken to treat the inside surfaces of the container, i.e. both the member and the covering film if necessary, for example by coating it with agents such as PVdC (poly)vinylidine dichloride) or PTFE (polytetrafluoroethylene) or to adapt the composition to ensure that it does not dissolve the polymer. For example, it has been found that ensuring the composition has a high ionic strength or contains an agent which minimises water loss through the walls of the container will prevent the composition from dissolving the polymer from the inside. This is described in more detail in EP-A-518,689 and WO 97/27743.

If more than one container is formed at the same time from the same sheet, the containers may then be separated from each other, for example by cutting the sealing portions, or flanges. Alternatively, they may be left conjoined and, for example, perforations or other means provided between the individual containers so that they can be easily separated a later stage, for example by a consumer. If the containers are separated, the flanges may be left in place. However, desirably the flanges are partially removed in order to provide an even more attractive appearance. Generally the flanges remaining should be as small as possible for aesthetic purposes while bearing in mind that some flange is required to ensure the two films remain adhered to each other. A flange having a width of 1 mm to 8 mm is desirable, preferably 2 mm to 7 mm, most preferably about 5 mm.

The containers may themselves be packaged in outer containers if desired, for example non-water soluble containers which are removed before the water-soluble containers are used.

The containers produced by the process of the present invention, especially when used for a fabric care, surface care or dishwashing composition, may have a maximum dimension of 5 cm, excluding any flanges. For example, a container may have a length of 1 to 5 cm, especially 3.5 to 4.5 cm, a width of 1.5 to 3.5 cm, especially 2 to 3 cm, and a height of 1 to 2 cm, especially 1.25 to 7.15 cm.

The invention claimed is:

1. A water-soluble container containing a composition, said container comprising a rigid framework having at least two openings positioned on different sides of the rigid framework, each opening being closed by a film wherein the rigid framework is in the form of a wire framework forming the edges of the container and wherein said composition is a dishwashing, fabric care, surface care, disinfectant, antibacterial, antiseptic or agricultural composition.

2. A container according to claim 1 wherein the rigid framework has been formed by moulding.

3. A container according to claim 2 wherein the rigid framework has been formed by injection moulding.

4. A container according to claim 1 wherein the film encloses the rigid framework.

5. A container according to claim 4 wherein the film has been wrapped around the rigid framework.

6. A container according to claim 5 wherein the film has been shrink-wrapped around the rigid framework.

7. A container according to claim 4 wherein the film has been thermoformed around the rigid framework.

8. A container according to claim 1 wherein the rigid framework comprises a poly(vinyl alcohol).

9. A container according to claim 1 wherein the film comprises a poly(vinyl alcohol).

10. A container according to claim 1 where the container comprises at least two compartments.

11. A container according to claim 10 wherein each compartment has an opening closed by a film.

12. A container according to claim 11 wherein the film over each opening has different dissolution characteristics.

13. A container according to claim 1 wherein the composition is a particulate solid, a gel or a liquid.

14. A container according to claim 1 wherein the composition is a dishwashing, water-softening, laundry or detergent composition or a rinse-aid.

15. A container according to claim 13 wherein the composition is a refill composition for a trigger spray.

16. A container according to claim 1 wherein the rigid framework is a cuboid.

17. A process for preparing the water-soluble container of claim 1 which comprises forming the framework having at least two openings on different sides, optionally closing at least one of the openings with a film, filling the framework with a composition and closing each remaining opening with a film.

* * * * *